United States Patent [19]

Saito et al.

[11] Patent Number: 4,655,899
[45] Date of Patent: Apr. 7, 1987

[54] PROBE ASSEMBLY FOR AN APPARATUS FOR MEASURING IONIC ACTIVITY

[75] Inventors: Yoshio Saito, Asaka; Osamu Seshimoto, Tokorozawa, both of Japan

[73] Assignee: Fuji Photo Film Co., Ltd., Kanagawa, Japan

[21] Appl. No.: 703,396

[22] Filed: Feb. 20, 1985

[30] Foreign Application Priority Data

Feb. 21, 1984 [JP] Japan .................................. 59-31082

[51] Int. Cl.[4] .............................................. G01N 27/46
[52] U.S. Cl. ........................................ 204/412; 204/416
[58] Field of Search ............... 204/406, 412, 416–420; 422/55, 100

[56] References Cited

U.S. PATENT DOCUMENTS

| 3,468,780 | 9/1969 | Fischer | 204/422 |
| 3,556,950 | 1/1971 | Dahms | 204/419 |
| 3,654,113 | 4/1972 | Bochinski | 204/419 |
| 4,053,381 | 10/1977 | Hamblen et al. | 204/418 |
| 4,332,658 | 6/1982 | Tsuboshima | 204/419 |
| 4,404,288 | 9/1983 | Huber | 204/434 |
| 4,437,970 | 3/1984 | Kitajima et al. | 204/412 |
| 4,506,226 | 3/1985 | Luce et al. | 204/406 |
| 4,517,071 | 5/1985 | Seshimoto | 204/1 T |

OTHER PUBLICATIONS

Fjeldly et al, "Solid-State Non-Selective Electrodes with Integrated Electronics", *J. Electrochem. Soc.*, May 1979, pp. 793–795.

Primary Examiner—T. Tung
Attorney, Agent, or Firm—Toren, McGeady and Goldberg

[57] ABSTRACT

A probe assembly has at least two pairs of probes and a relay for switchably connecting any one pair of the probes to a single electric impedance lowering means. When the pairs of probes are brought into contact with terminals of at least two pairs of ion-selective electrodes of an ionic activity device, the potential difference generated between each pair of said electrodes is successively transferred to a measuring means by way of the electric impedance lowering means.

5 Claims, 6 Drawing Figures

PROBE ASSEMBLY FOR AN APPARATUS FOR MEASURING IONIC ACTIVITY

BACKGROUND OF THE INVENTION

1. Field of the Invention

This invention relates to a probe assembly (or a potential detector) for an apparatus for measuring ionic activity. In the present invention, "an apparatus for measuring ionic activity" refers to an apparatus (i.e. an electrolyte analyzer) for potentiometrically measuring the ionic activities of electrolyte ions contained in aqueous liquid samples, for example, body fluids (e.g. whole blood, blood plasma, blood serum, and urine), liquor, and drinking water, and of a product formed by the reaction among the components contained in a liquid.

More particularly, this invention relates to an improvement in a probe assembly having at least two pairs of probes which come into contact with terminals of at least two pairs of ion-selective solid state electrodes of an ionic activity measuring device, each of said pairs of electrodes having an ion-selective layer sensitive to a predetermined specific ion, so as to measure the potential difference generated between each of said electrodes of each pairs of electrodes corresponding to ionic activity difference existing as to a specific ion between reference and sample solutions spotted on said ionic activity measuring device, the improvement being to function to prevent potential deviation resulting from cross talk interference between the pairs of electrodes and to minimize the influence of electrical noise on the measured potential.

2. Description of the Prior Art

Measurement of the ionic activity of an electrolyte ion, for example, $Na^+$, $K^+$, $Cl^-$, $Ca^{2+}$, $HCO_3^-$-(or $CO_3^{2-}$), or the like, has significant importance in clinical chemistry tests. As the main methods for measuring ionic activity, there are known such techniques as flame analysis in which a sample solution is injected into a flame to determine the ionic activity on the basis of the wavelength of the light thus generated, coulometry in which electrolysis is conducted in the sample solution to determine the ionic activity on the basis of the quantity of electricity produced, and potentiometry in which an ion-selective electrode is used to determine the ionic activity on the basis of the potential generated in proportion to the logarithm of the ionic activity of a specific ion contained in a sample solution supplied to said electrode. Among these methods, potentiometry has attracted much attention in recent years, since it is safer, quicker, and more convenient than flame analysis or coulometry.

In the potentiometric measurement of ionic activity, an ionic activity measuring device having ion-selective electrodes is utilized. As such a device, a dry slide-type device having a pair of film-like planar ion-selective electrodes is disclosed (for example, by Japanese unexamined Patent publication No. 52(1977)-142584, and U.S. Pat. Nos. 4,053,381 and 4,437,970). The basic structure of this ionic activity measuring device is that of a slide comprising at least one pair of solid state electrodes each having an outermost ion-selective layer and a porous bridge which can promote capillary action between a pair of said ion-selective layers. By spotting a reference solution on one layer of said pair of ion-selective layers and a sample solution on the other, and then measuring the potential difference between the electrodes, the ionic activity of a specific ion contained in the sample solution can be determined. Such a device having at least two pairs of ion-selective solid state electrodes is particularly preferable since it enables different kinds of ions to be measured simultaneously or successively.

Using the foregoing ionic activity measuring device, spotting of reference and sample solutions, measurement of potential difference and conversion of the measured potential difference into ionic activity are conducted in the apparatus for measuring ionic activity disclosed in Japanese patent application Ser. No. 59(1984)-12796.

In this apparatus, at least one pair of probes come into contact with terminals of at least one pair of ion-selective electrodes of the ionic activity measuring device so as to output the potential difference between the ion-selective electrodes to a measuring circuit. An example of a probe assembly having such a pair of probes is disclosed in Japanese unexamined patent publication No. 59(1984)-188550. By using such a probe assembly in the apparatus for measuring ionic activity, it has been possible to measure potential differences easily and rapidly.

However, such potential differences are extremely small, namely, in the order of from several tens of milli volts to a hundred and several tens of milli volts. On the other hand, the electrical resistance of the electrodes is extremely high, sometimes more than $10^8$–$10^9\Omega$. Accordingly, impedance of the potential difference signal is so high that, any electrical noise mixing in with the potential difference signal in a circuit (or line) between where the probes contact the electrodes and the measuring circuit, can cause a great deterioration in S/N ratio of the signal, resulting in incorrect measurement. Particularly, when the number of probes is increased to measure different kinds of ions simultaneously (or successively), the deterioration of S/N ratio is likely to become marked since there may be electrical interference, or electrical noise between the circuits (or lines) from the probes to the measuring circuit.

For this reason, the probe assembly may be connected to a appropriate electric impedance lowering means, but if one electric impedance lowering means is connected to two or more pairs of probes, there tends to be great deviation of the measured potential due to the electric interference that is produced.

SUMMARY OF THE INVENTION

It is thus an object of the present invention to provide a probe assembly (or potential difference detector) having at least two pairs of probes which can obtain good potential difference signals substantially free of electrical interference and little influenced by electric noise.

The probe assembly (or potential difference detector) in accordance with the present invention is characterized in that it has at least two pairs of probes each of which comes into contact with the terminals of at least two pairs of ion-selective solid state electrodes of an ionic activity measuring device, and a relay for switchably connecting any one pair of said probes to a single electric impedance lowering means.

Since the probe assembly in accordance with the present invention not only functions to transfer potential of ion-selective electrodes to the potential difference measuring circuit, but also has an electric circuit including a relay which can measure the potential difference with a high S/N ratio, it can be referred to as a potential difference detector.

In the present invention, "an electric impedance lowering means" refers to any means which functions to lower the electric impedance of the detected potential difference signal with or without gain. In order to minimize noise, it is preferable to dispose the electric impedance lowering means as near to the probe assembly as possible. However, said means can be disposed away from the probe assembly, for example, it may be a component of the potential difference measuring circuit of an apparatus for measuring ionic activity.

In the present invention, a "relay" refers to any means which can automatically make and break a circuit while maintaining a micro potential at a high S/N ratio including, for example, a contact type relay, a relay circuit comprising semiconductors, an automatic control circuit using these relays, and the like. The aforesaid disposition of the electric impedance lowering means also applies to the disposition of the relay.

The pairs of probes are successively connected to a single electric impedance lowering means by the relay in the probe assembly in accordance with the present invention, and there is none of the interference between pairs of electrodes which could greatly alter the potential difference, and the potential difference signal having a superior S/N ratio can be detected without any electrical interference in the circuit between the probes and the potential difference measuring circuit. Particularly, when the relay and a preamplifier (i.e. an electric impedance lowering means) are associated with the probe assembly or disposed in the vicinity of the probes, the S/N ratio can be further improved since the invasion of noise along a path which extends from the probes to the preamplifier by way of the relay is greatly decreased. Thus, by using the probe assembly in accordance with the present invention, the ionic activity of different kinds of ions can be measured rapidly and accurately.

DESCRIPTION OF THE PREFERRED EMBODIMENTS

Figure 1:
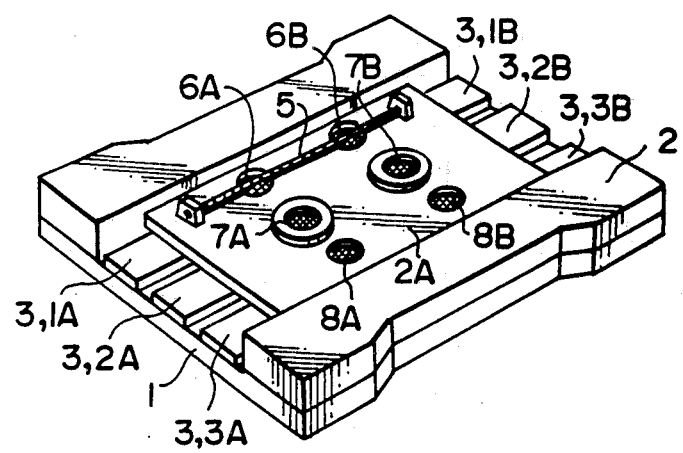
FIG. 1 is a perspective view of an example of a potentiometric ionic activity measuring device to which the probe assembly in accordance with the present invention is applicable.

FIG. 1 is a perspective view of an example of slide-type ionic activity measuring device (hereinafter referred to as a "slide") to which the probe assembly in accordance with the present invention is applicable. The slide here comprises a lower slide frame 1, an upper slide frame 2, and three pairs of ion-selective electrodes 3.1A,3.1B; 3.2A,3.2B; and 3.3A,3.3B; each of said pairs having an outermost ion-selective layer (not shown) and being disposed between said lower and upper slide frames 1 and 2. Three pairs of through holes 6A,6B; 7A,7B; and 8A,8B are formed in the center portion 2A of the upper slide frame 2. These through holes are functionally divided into a pair of apertures for liquid-spotting 7A and 7B (for a reference solution and for a sample solution, respectively), and two pairs of vent apertures 6A,6B and 8A,8B. The liquid spotted on the aperture 7A diffuses into the vent apertures 6A and 8A, and the liquid spotted on the aperture 7B diffuses into the vent apertures 6B and 8B, by way of porous liquid-distribution members (i.e. bandage cloth or gauze, not shown). A porous bridge (spun yarn bridge) 5 which can promote capillary action is disposed on the vent apertures 6A and 6B. The ends of said bridge 5 are fixed on the upper slide frame 2. The liquids hemispherically rise from the vent apertures 6A and 6B penetrate the porous bridge 5 so that their interfaces meet within said bridge, thus forming an electrical conduction therebetween.

Each pair of said ion-selective electrodes may have a different ion-selectivity, for example, the electrodes 3.1A and 3.1B for $Na^+$; 3.2A and 3.2B for $K^+$; and 3.3A and 3.3B for $Cl^-$, so that the potential difference corresponding to each of the said ions is measured between each pair of said electrodes.

The ionic activity measuring device shown in FIG. 1 which can measure ionic activity of different types of ions is disclosed in, for example, U.S. Pat. No. 4,437,970 and Japanese patent application Ser. No. 59(1984)-11744.

Figure 2A:
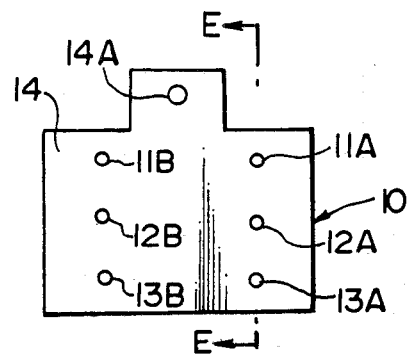
FIG. 2A is a plan view of an embodiment of the probe assembly in accordance with the present invention.
Figure 2B:
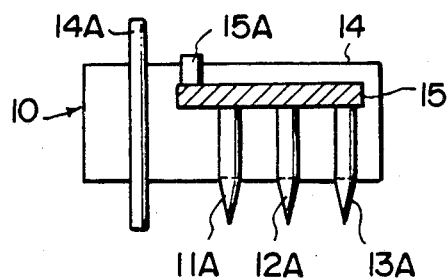
FIG. 2B is a sectional side view of said embodiment of the probe assembly taken along the line E—E of FIG. 2A.
Figure 2C:
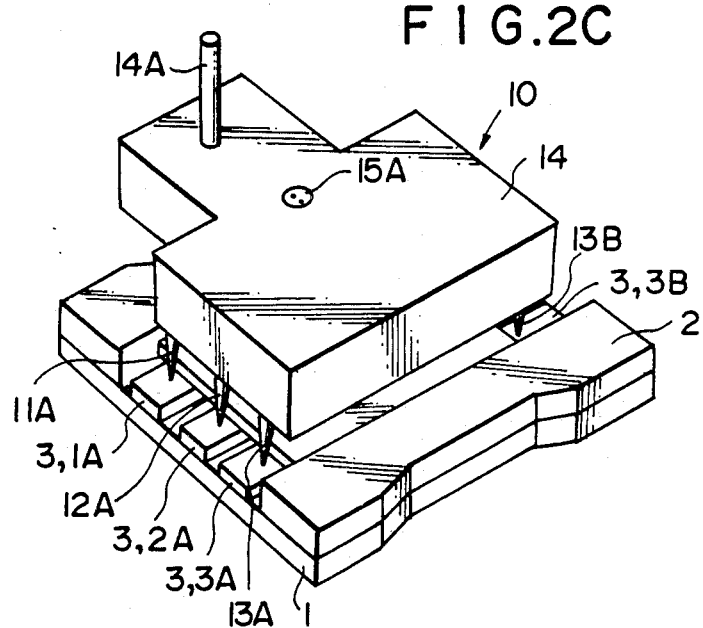
FIG. 2C is a perspective view of said embodiment of the assembly brought into contact with the ionic activity measuring device shown in FIG. 1.

FIGS. 2A, 2B and 2C are, respectively, a plan view of an embodiment of the probe assembly in accordance with the present invention, a sectional side view taken along the line E—E of said plan view, and a perspective view of said embodiment of the probe assembly brought into contact with said ionic activity measuring device.

The probe assembly 10 represented by these drawings comprises three pairs of probes (11A and 11B; 12A and 12B; and 13A and 13B) united by a support member 14, and is supported, by means of a support rod 14A, in an apparatus for measuring ionic activity (not shown) so as to be vertically movable. Within the support member 14, a substrate 15 is disposed in contact with said probes. This substrate incorporates a preamplifier circuit for connecting with the three pairs of probes via relays which are controlled by means of a control circuit.

Figure 3:
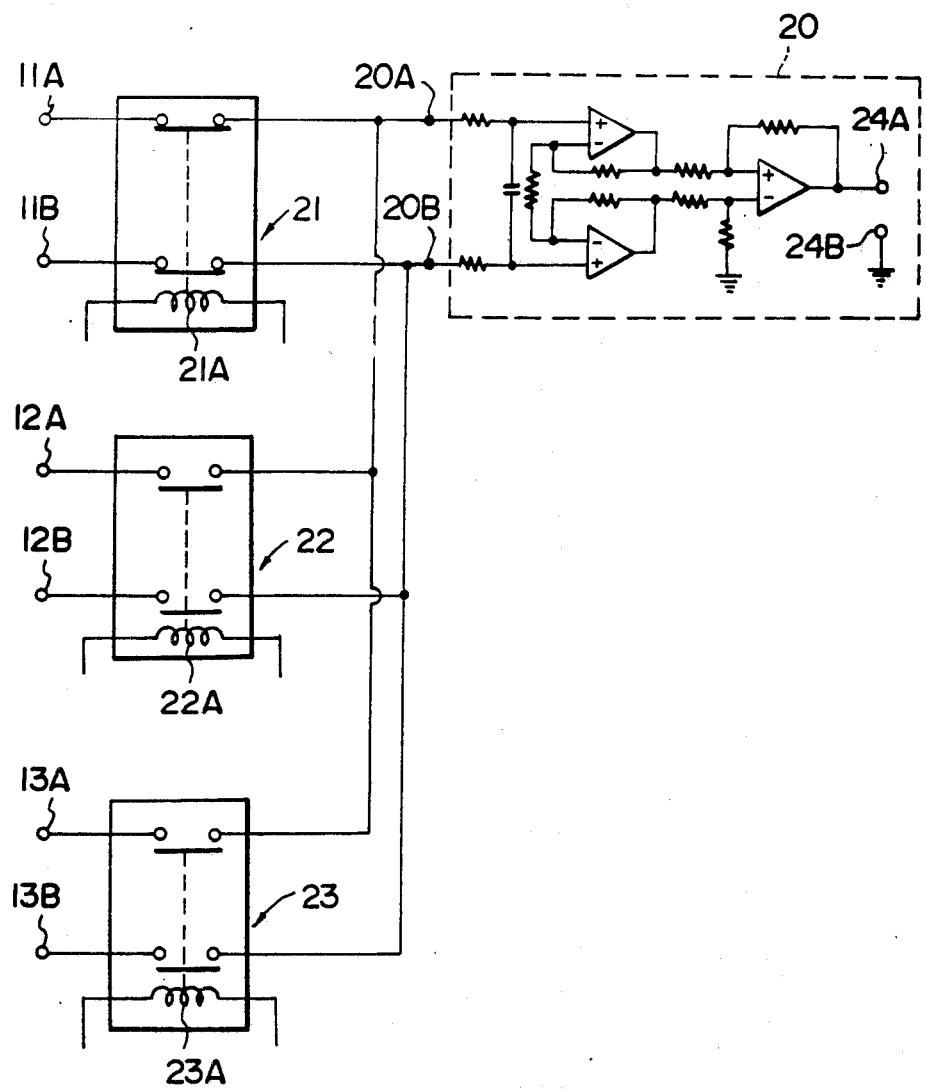
FIG. 3 is a circuit diagram of an example of a circuit comprising the electric impedance lowering means, relays and probes used in said embodiment.

FIG. 3 is a circuit diagram of an example of the preamplifier circuit and relays which are incorporated in the substrate 15. In this example, input ends 20A and 20B of the preamplifier circuit 20 can be connected, by way of relays 21, 22 and 23, to any one pair of probes 11A,11B; 12A,12B; and 13A,13B (in this Figure, they are connected to the pair of probes 11A and 11B). Output ends 24A and 24B are connected to the input ends of the potential difference measuring circuit of an apparatus by way of an output terminal portion consisting of, for example, connectors.

The functioning of the aforesaid probe assembly in the apparatus for measuring ionic activity will now be described hereinbelow.

A reference solution and a sample solution are spotted on the aperture for liquid-spotting 7A and the aperture for liquid-spotting 7B, respectively, in the slide of FIG. 1, at a spotting portion of the apparatus.

After the spotting, the slide is conveyed within the said apparatus to a measuring portion of an incubation portion where the probe assembly in accordance with the present invention is supported in a vertically movable way. When the slide reaches the measuring point, the probe assembly is moved vertically by a known driving means so that each probe comes into contact with a terminal portion of each electrode of the slide as shown in FIG. 2C. In this Figure, the probes 11A, 11B, 12A, 12B, 13A and 13B are in contact with the electrodes 3.1A, 3.1B, 3.2A, 3.2B, 3.3A and 3.3B, respectively. If the electrodes 3.1A and 3.1B function as ion-selective electrodes for $Na^+$, the potential difference corresponding to the ionic activity difference of $Na^+$ between reference and sample solutions generated between said electrodes 3.1A and 3.1B is conducted by means of the probes 11A and 11B, and similarly, the potential difference corresponding to ionic activity of other ions (e.g. $K^+$ and $Cl^-$) is conducted by means of pairs of probes 12A,12B and 13A,13B.

By controlling at this point the relays 21, 22 and 23 shown in FIG. 3 using a known means, the potential differences are successively inputted to the preamplifier 20 through input ends 20A and 20B.

Figure 4:
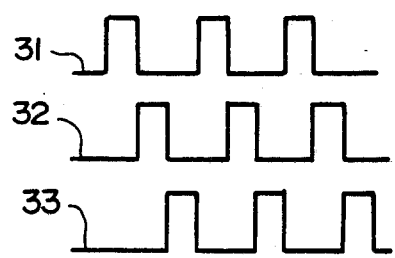
FIG. 4 is a schematic diagram of a set of pulse signals for controlling the relays shown in FIG. 3.

FIG. 4 is a schematic view of an example of a set of pulse signals for controlling said relays. For example, pulse signals 31, 32 and 33 are supplied to electromagnetic coils 21A, 22A and 23A of the relays 21, 22 and 23, respectively, so that said potential difference is inputted to the preamplifier 20. However, in place of the pulse signals, an electric current for closing a relay contacts can be supplied successively to the electromagnetic coils 21A, 22A and 23A by a manual rotary switch, a programmed control circuit, or the like, disposed in an operating portion of the apparatus, to control the relays.

The potential difference is amplified by the preamplifier 20 and inputted to the potential difference measuring circuit of the apparatus from the output ends 24A and 24B.

The probe assembly for an apparatus for measuring ionic activity in accordance with the present invention is not limited by the foregoing embodiment, but may take various other forms.

For example, the slide may be conveyed with its apertures for liquid-spotting facing down. In this case, the probe assembly may be moved upwardly from below with its probes projecting up so as to come into contact with the terminals of said slide.

Also, as described in Japanese unexamined patent publication No. 59(1984)-188550, probes may be configured to resiliently come into contact with the electrodes so as to lower electric contact resistance, for obtaining a favorable measurement.

Further, though the foregoing embodiment is directed to a unit comprising a probe assembly, relays and a preamplifier, the present invention encompasses an embodiment in which these components are separated but are close enough to each other that they can be regarded substantially as a unit.

We claim:

1. An apparatus for measuring the potential difference of each pair of ion-selective solid state electrodes of a slide ionic activity measuring device wherein each of said electrodes has a terminal exposed from at least either of the upper and lower surfaces of said ionic activity measuring device, said apparatus comprising at least two pairs of probes which are vertically movable and are arranged so as to simultaneously come into contact with the respective terminals of said electrodes; an electric impedance lowering means; and a relay for switchably connecting any one pair of said probes to the electric impedance lowering means.

2. The apparatus of claim 1 wherein said electric impedance lowering means is a preamplifier circuit.

3. The apparatus of claim 1 wherein said relay and said electric impedance lowering means are incorporated into a circuit on a substrate which is in contact with said probes.

4. The apparatus of claim 1 wherein said relay is connected by a pulse signal outputted from a controlling means.

5. The apparatus of claim 1 wherein said probes are resiliently projected.

* * * * *